(12) United States Patent
Murata

(10) Patent No.: US 12,156,638 B2
(45) Date of Patent: Dec. 3, 2024

(54) MEDICAL DEVICE AND TREATMENT SYSTEM

(71) Applicant: OLYMPUS CORPORATION, Tokyo (JP)

(72) Inventor: Takeshi Murata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 922 days.

(21) Appl. No.: 17/163,834

(22) Filed: Feb. 1, 2021

(65) Prior Publication Data

US 2021/0251468 A1 Aug. 19, 2021

Related U.S. Application Data

(63) Continuation of application No. PCT/JP2018/029788, filed on Aug. 8, 2018.

(51) Int. Cl.
*A61B 1/008* (2006.01)
*A61B 1/005* (2006.01)
*A61B 1/01* (2006.01)

(52) U.S. Cl.
CPC ............ *A61B 1/008* (2013.01); *A61B 1/0057* (2013.01); *A61B 1/01* (2013.01)

(58) Field of Classification Search
CPC ......... A61B 1/008; A61B 1/0057; A61B 1/01; A61B 1/0052; A61B 1/0055; A61B 1/00078
See application file for complete search history.

(56) References Cited

U.S. PATENT DOCUMENTS

2012/0046522 A1\* 2/2012 Naito .................. A61B 1/0052
600/118
2013/0041224 A1\* 2/2013 Okaniwa .............. A61B 1/0056
600/142
2015/0342722 A1 12/2015 Balasubramanian et al.
(Continued)

FOREIGN PATENT DOCUMENTS

EP 2 517 613 A1 10/2012
JP 01-120805 U 8/1989
JP 06-066619 U 9/1994
(Continued)

OTHER PUBLICATIONS

International Search Report dated 9, 2018 received in PCT/JP2018/029788.

*Primary Examiner* — Aaron B Fairchild
(74) *Attorney, Agent, or Firm* — Scully, Scott, Murphy & Presser, P.C.

(57) ABSTRACT

A medical device includes an insertion unit; and a drive unit, the insertion unit has first, second and third lumens, the drive unit has first and second pulleys disposed to be movable advance and retraction, first and second wires are wound on the first and second pulleys, respectively, and a pulling mechanism to pull the first and second pulleys toward a proximal end side, the first wire has a first end inserted into the first lumen and fixed to a distal end side of the insertion unit and a second end inserted into the second lumen and fixed to the distal end side of the insertion unit, and the second wire has a first end inserted into the third lumen and fixed to the distal end side of the insertion unit and a second end fixed to the drive unit.

19 Claims, 8 Drawing Sheets

(56) References Cited

U.S. PATENT DOCUMENTS

2018/0271354 A1* 9/2018 Tilson ............... A61M 25/0105

FOREIGN PATENT DOCUMENTS

| JP | 2006-512935 A | 4/2006 |
|----|---------------|--------|
| JP | 2010-000360 A | 1/2010 |
| WO | 03/105671 A2 | 12/2003 |
| WO | 2011/114568 A1 | 9/2011 |
| WO | 2017/195328 A1 | 11/2017 |

* cited by examiner

MEDICAL DEVICE AND TREATMENT SYSTEM

This application is a continuation application based on a PCT International Application No. PCT/JP2018/029788, filed on Aug. 8, 2018, content of the PCT International Application is incorporated herein by reference.

BACKGROUND OF THE INVENTION

Field of the Invention

Description of Related Art

In the related art, an overtube that assists with treatment of inserting a medical device such as an endoscope or a treatment tool into a body cavity or a lumen, for example, a deep portion of the large intestine or the small intestine, is known. The overtube is flexible and has a lumen (a channel or a duct) into which a medical device such as an endoscope and a treatment tool can be inserted.

An insertion unit of the medical device is inserted into the lumen of the overtube and is inserted into the body cavity or the lumen together with the overtube. Further, when the overtube is first inserted into the body cavity or the lumen, the insertion unit of the medical device is inserted along the lumen of the overtube.

In this way, the overtube functions as a guide for the insertion unit of the medical device. As a result, even in a case where the body cavity or the lumen has a bent portion, the insertion unit of the medical device can be smoothly inserted into the deep portion of the body cavity or the lumen.

Patent Document 1 discloses an overtube having a shape lock function. A part of the overtube described in Patent Document 1 is constituted by a plurality of nested elements (pieces). When a wire inserted into the plurality of nested elements is pulled toward a proximal end side in a longitudinal axis direction of the overtube, the close contact force between the nested elements increases. As a result, the shape of the overtube is temporarily fixed due to the frictional force generated between the nested elements.

In the overtube in which the shape of the overtube is temporarily fixed, when an affected portion in a flexible body cavity or lumen is treated, it is possible to stably dispose a medical device such as an endoscope or a treatment tool. Further, in the overtube in which the shape of the overtube is temporarily fixed, it is possible to more reliably guide a distal end of the treatment tool to a distal end of the overtube.

In the overtube described in Japanese Unexamined Patent Application, First Publication No. 2006-512935, four wires are inserted into the plurality of nested elements. The length of a path of the wire which is inserted into the overtube (hereinafter referred to as "a path length") changes depending on the bending posture of the overtube. Since the paths of the four wires are symmetrically disposed with respect to the central axis of the nested elements, the total value of the path lengths of the two opposing wires does not change. Therefore, it is easy to find the pull lengths of the wires to evenly pull the four wires.

SUMMARY OF THE INVENTION

To solve the above problem, the present invention proposes the following means.

A medical device according to a first aspect of the present invention includes a long insertion unit that is inserted into a body; and a drive unit provided on a proximal end side of the insertion unit, wherein the insertion unit has a first lumen, a second lumen, and a third lumen which are disposed at intervals in a circumferential direction around a longitudinal axis of the insertion unit, wherein the drive unit has a first pulley disposed to be movable advance and retraction, a second pulley disposed to be movable advance and retraction, a first wire wound on the first pulley, a second wire wound on the second pulley, and a pulling mechanism that is configured to pull the first pulley and the second pulley toward a proximal end side, wherein the first wire has a first end that is inserted into the first lumen and fixed to a distal end side of the insertion unit and a second end that is inserted into the second lumen and fixed to the distal end side of the insertion unit, and wherein the second wire has a first end that is inserted into the third lumen and fixed to the distal end side of the insertion unit and a second end that is fixed to the drive unit.

According to a second aspect of the present invention, in the medical device according to the first aspect, the first lumen, the second lumen, and the third lumen are disposed at equal intervals in the circumferential direction around the longitudinal axis, and distances from the longitudinal axis to the first lumen, the second lumen, and the third lumen are equal to each other.

According to a third aspect of the present invention, in the medical device according to the second aspect, the first pulley and the second pulley is configured to move advance and retraction with bending of the insertion unit, and a movement amount of the first pulley and a movement amount of the second pulley are substantially equal to each other.

According to a fourth aspect of the present invention, in the medical device according to the first aspect, the pulling mechanism has a third pulley disposed to be movable advance and retraction, and a third wire wound on the third pulley, wherein the third wire has a first end that is fixed to the first pulley and a second end that is fixed to the second pulley, and wherein the third pulley is configured to moves advance and retraction to pull the first wire and the second wire.

According to a fifth aspect of the present invention, in the medical device according to the first aspect, the insertion unit includes a variable stiffness portion, the stiffness of which is configured to change with a compressive force in a longitudinal axis direction, and wherein both ends of the first wire and the first end of the second wire are fixed to a distal end side of the variable stiffness portion.

According to a sixth aspect of the present invention, in the medical device according to the first aspect, the variable stiffness portion has a plurality of pieces into which the first wire and the second wire are inserted and which is movable in the longitudinal axis direction, and wherein, when the first wire and the second wire are pulled toward the proximal end side and the plurality of pieces are brought into close contact with each other, the stiffness of the variable stiffness portion changes.

A treatment system according to a seventh aspect of the present invention includes an endoscope; and the above described medical device, a multi-lumen tube having a fourth lumen into which the endoscope can be inserted, a fifth lumen, and a sixth lumen; wherein the insertion unit of the medical device has a main lumen into which the multi-lumen tube can be inserted.

According to an eighth aspect of the present invention, an endoscope; and the above described medical device, wherein the insertion unit of the medical device includes a fourth lumen into which the endoscope can be inserted, a fifth lumen, and a sixth lumen.

According to a ninth aspect of the present invention, in the treatment system according to the eighth aspect, wherein, in a cross section perpendicular to the longitudinal axis direction of the insertion unit, the fifth lumen and the sixth lumen are disposed symmetrically with respect to an axis passing through a center of the fourth lumen and a center of any one of the first lumen, the second lumen, and the third lumen, and any two of the first lumen, the second lumen, and third lumen which are not on the axis are symmetrically disposed with respect to the axis.

According to a tenth aspect of the present invention, in the treatment system according to the ninth aspect, wherein, in a cross section perpendicular to the longitudinal axis direction of the insertion unit, the center of each of the fourth lumen, the fifth lumen, and the sixth lumen is disposed in any one of a first region defined between a line segment connecting the first lumen and the longitudinal axis of the insertion unit and a line segment passing through the second lumen and the longitudinal axis of the insertion unit, a second region defined between a line segment connecting the first lumen and the longitudinal axis of the insertion unit and a line segment passing through the third lumen and the longitudinal axis of the insertion unit, and a third region defined between a line segment connecting the second lumen and the longitudinal axis of the insertion unit and a line segment passing through the third lumen and the longitudinal axis of the insertion unit.

BRIEF DESCRIPTION OF THE DRAWINGS

FIG. 4 shows the insertion unit of the overtube, in which FIG. 4(a) is a cross-sectional view of the insertion unit and FIG. 4(b) is a side view of the insertion unit.

DETAILED DESCRIPTION OF THE INVENTION

First Embodiment

A first embodiment of the present invention will be described with reference to FIGS. 1 to 9.

Figure 1:
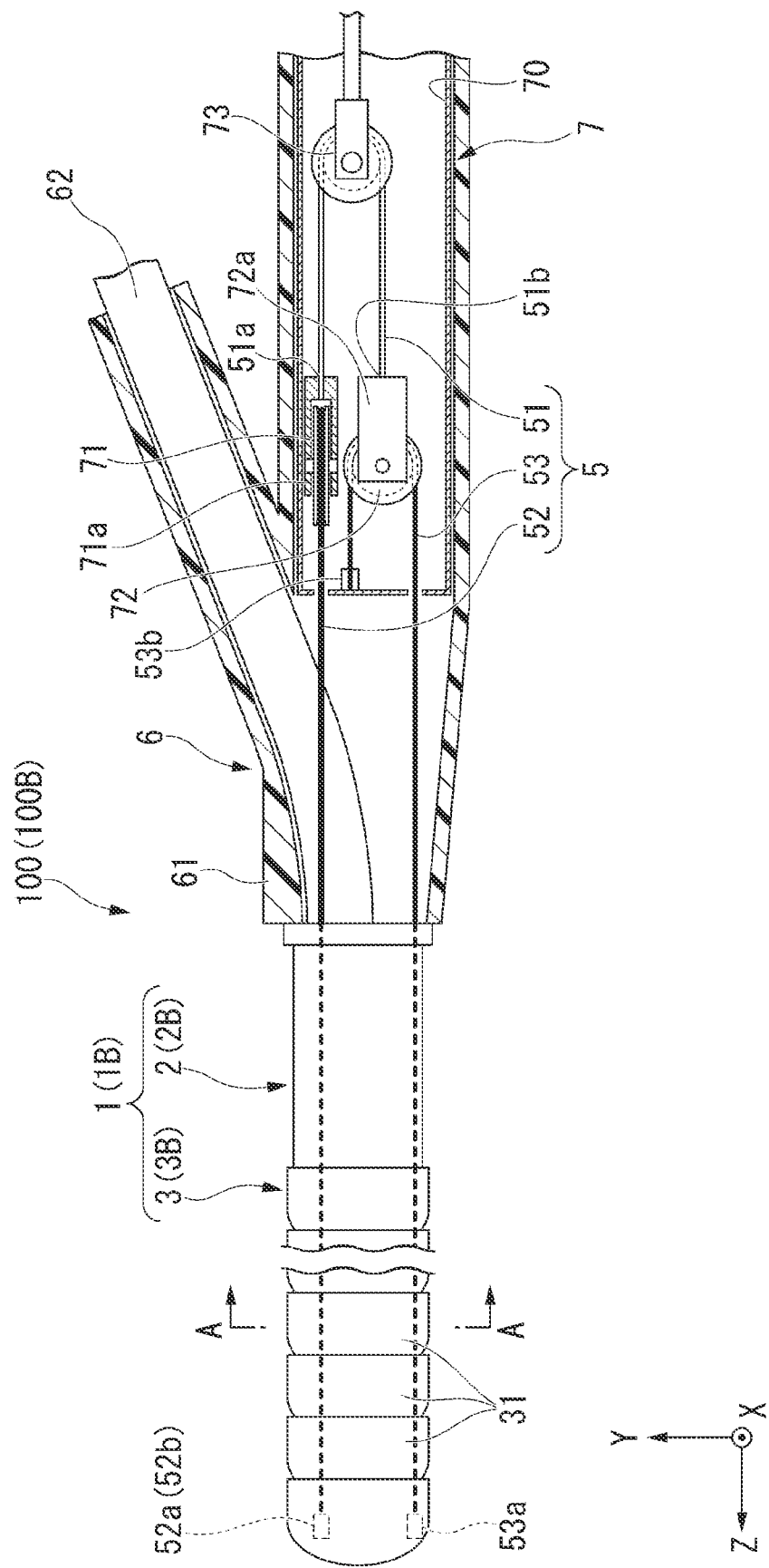
FIG. 1 is a diagram showing an overall configuration of an overtube according to a first embodiment of the present invention.

FIG. 1 is a diagram showing an overall configuration of an overtube 100 according to the present embodiment.

[Overtube (Medical Device) 100]

An overtube (a medical device) 100 includes an insertion unit 1, an operation unit 6 provided at a proximal end of the insertion unit 1, and a drive unit 7 having a third wire 51, a first wire 52, and a second wire 53.

The insertion unit 1 is a long member that is inserted into the body. The insertion unit 1 has a bendable bending portion 3 provided on a distal end side thereof and a flexible tube portion 2 that is connected to the bending portion 3 and extends to a proximal end side thereof.

The flexible tube portion 2 is a tubular member formed of a flexible material such as silicone and has a main lumen 2a into which a multi-lumen tube 200 that will be described later is inserted.

As shown in FIG. 1, the bending portion (a variable hardness portion) 3 is constituted by a plurality of bending pieces 31 disposed side by side in an axial direction and is provided at a distal end of the flexible tube portion 2. The stiffness of the bending portion 3 changes with a compressive force in a longitudinal axis direction.

The bending piece 31 is a short cylindrical member and an internal space thereof is open at both ends. The plurality of bending pieces 31 are superposed such that the internal spaces of the adjacent bending pieces 31 form a continuous space. A multi-lumen tube 200 which will be described later is inserted into the continuous internal space.

Figure 2:
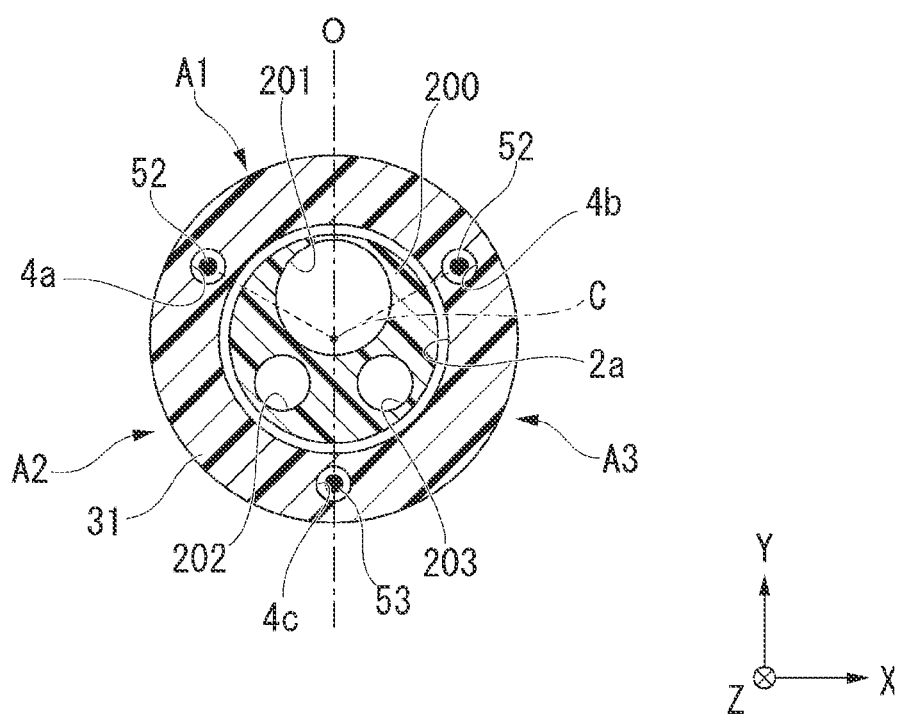
FIG. 2 is a cross-sectional view of an insertion unit of the overtube.

FIG. 2 is a cross-sectional view perpendicular to the longitudinal axis of the bending portion 3 of the insertion unit 1. In the following description, an A-A cross section is also referred to as an XY plane, and the longitudinal axis direction of the insertion unit 1 is also referred to as a Z axis direction. A multi-lumen tube 200 which will be described later is inserted into the internal space of the insertion unit 1 shown in FIG. 2.

As shown in FIG. 2, three wire lumens 4 (a first lumen 4a, a second lumen 4b, and a third lumen 4c) are disposed in the insertion unit 1 (the flexible tube portion 2 and the bending portion 3) at intervals in a circumferential direction around the longitudinal axis of the insertion unit 1. The three wire lumens 4 are internal spaces into which the three wires (the third wire 51, the first wire 52, and the second wire 53) can each be inserted. As shown in FIG. 2, the three wire lumens 4 are disposed at positions where a circumference around the longitudinal axis of the insertion unit 1 is substantially equally divided. Further, distances from the central axis C to the three wire lumens 4 are substantially the same.

The first wire 52 and the second wire 53 are inserted into the wire lumen 4 of all the bending pieces 31 and the flexible tube portion 2.

Since the first wire 52 and the second wire 53 are inserted into all the bending pieces 31, the bending pieces 31 are not separated from each other. By moving the bending pieces 31 relative to the adjacent bending pieces 31, it is possible to bend the entire bending portion 3.

As shown in FIG. 1, the operation unit 6 has an operation unit main body 61 to which the proximal end side of the flexible tube portion 2 is connected and an insertion port 62.

The operation unit main body 61 is a tubular member formed of a highly rigid material, as shown in FIG. 1, has an outer diameter larger than the outer diameter of the flexible tube portion 2, and is formed in a shape that can be easily grasped by the operator.

As shown in FIG. 1, an insertion port 62 through which the multi-lumen tube 200 that will be described later is inserted is provided on the outer periphery of the operation unit main body 61. The insertion port 62 of the operation unit main body 61 communicates with the internal space of the flexible tube portion 2.

The drive unit 7 is provided on the proximal end side of the insertion unit 1 and pulls the third wire 51, the first wire 52, and the second wire 53 toward the proximal end side. As shown in FIG. 1, the drive unit 7 has the third wire 51, the first wire 52, the second wire 53, a drive unit main body 70, a first pulley 71, a second pulley 72, and a third pulley 73.

As shown in FIG. 1, the drive unit main body 70 is formed integrally with the operation unit 6 and is provided with the first pulley 71, the second pulley 72, and the third pulley 73 inside. The position of the drive unit main body 70 relative to the insertion unit 1 is fixed.

The first pulley 71 is supported to be movable advance and retraction with respect to the drive unit main body 70. Specifically, a rotation shaft of the first pulley 71 is movably supported in a direction perpendicular to a rotation shaft direction. The rotation shaft of the first pulley 71 is perpendicular to the longitudinal axis of the insertion unit 1.

The second pulley 72 is supported to be movable advance and retraction with respect to the drive unit main body 70. Specifically, a rotation shaft of the second pulley 72 is movably supported in a direction perpendicular to a rotation shaft direction. The rotation shaft of the second pulley 72 is perpendicular to the longitudinal axis of the insertion unit 1 and the rotation shaft of the first pulley 71.

The third pulley 73 is supported to be movable advance and retraction with respect to the drive unit main body 70. Specifically, a rotation shaft of the third pulley 73 is movably supported in a direction perpendicular to a rotation shaft direction. The third wire 51 is wound on the third pulley 73. A first end 51a which is a first end of the third wire 51 is fixed to the rotation shaft of the first pulley 71 via a first pulley support member 71a. A second end 51b which is a second end of the third wire 51 is fixed to the rotation shaft of the second pulley 72 via a second pulley support member 72a.

The third pulley 73 is disposed to be closer to a proximal end side than the first pulley 71 and the second pulley 72. When the third pulley 73 is pulled with respect to the drive unit main body 70, the first pulley 71 and the third pulley 73 to which both ends of the third wire 51 are fixed are pulled in the same direction.

The first wire 52 is wound on the first pulley 71. As shown in FIG. 2, the first wire 52 is inserted into the first lumen 4a and the second lumen 4b. A first end 52a which is a first end of the first wire 52 is inserted into the first lumen 4a and fixed to the distal end side of the insertion unit 1. A second end 52b which is a second end of the first wire 52 is inserted into the second lumen 4b and fixed to the distal end side of the insertion unit 1.

The second wire 53 is wound on the second pulley 72. As shown in FIG. 2, the second wire 53 is inserted into the third lumen 4c. A first end 53a which is a first end of the second wire 53 is inserted into the third lumen 4c and fixed to the distal end side of the insertion unit 1. A second end 53b which is a second end of the second wire 53 is fixed to the drive unit main body 70.

Figure 3:
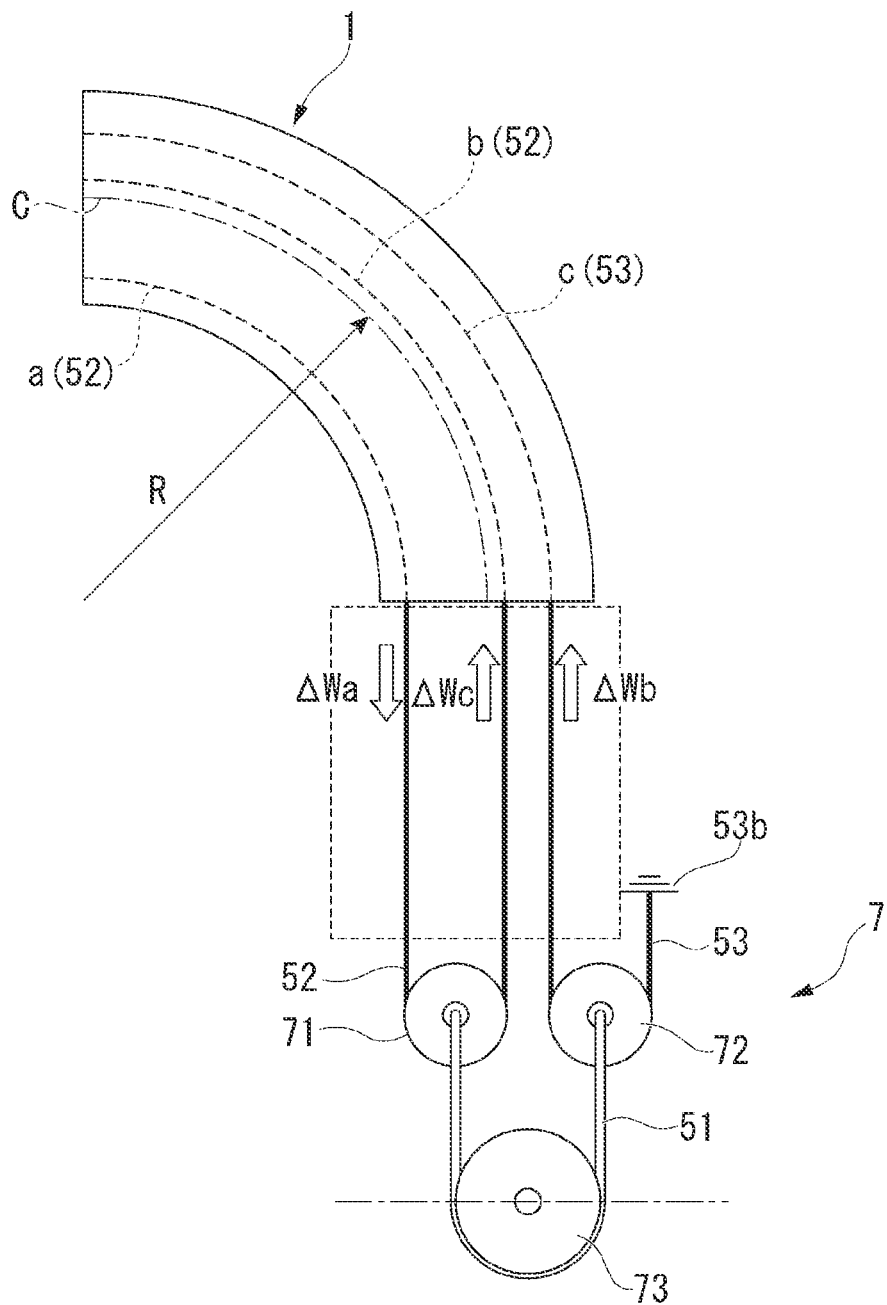
FIG. 3 is a schematic view of the insertion unit, a wire, and a drive unit of the overtube.

FIG. 3 is a schematic view of the insertion unit 1 and the drive unit 7.

Here, the first wire 52 that is inserted into the first lumen 4a is defined as "a wire a," the first wire 52 that is inserted into the second lumen 4b is defined as "a wire b," and the second wire 53 that is inserted into the third lumen 4c is defined as "a wire c."

Further, a change amount in a path length of the wire a that is inserted into the insertion unit 1, which is caused by the bending of the insertion unit 1, is defined as "$\Delta Wa$." Similarly, a change amount in a path length of the wire b that is inserted into the insertion unit 1, which is caused by the bending of the insertion unit 1, is defined as "$\Delta Wb$." Similarly, a change amount in a path length of the wire c that is inserted into the insertion unit 1, which is caused by the bending of the insertion unit 1, is defined as "$\Delta Wc$."

In an example shown in FIG. 3, the path length of the wire a that is inserted into the insertion unit 1 is shorter than the length of the central axis C of the insertion unit 1. On the other hand, the path length of each of the wire b and the wire c that are inserted into the insertion unit 1 is longer than the length of the central axis C of the insertion unit 1. Therefore, $\Delta Wa$, $\Delta Wb$, and $\Delta Wc$ are different and a wire pulling amount to evenly pull the three wires (the wire a, the wire b, and the wire c) is different for each of the three wires.

Figure 4:
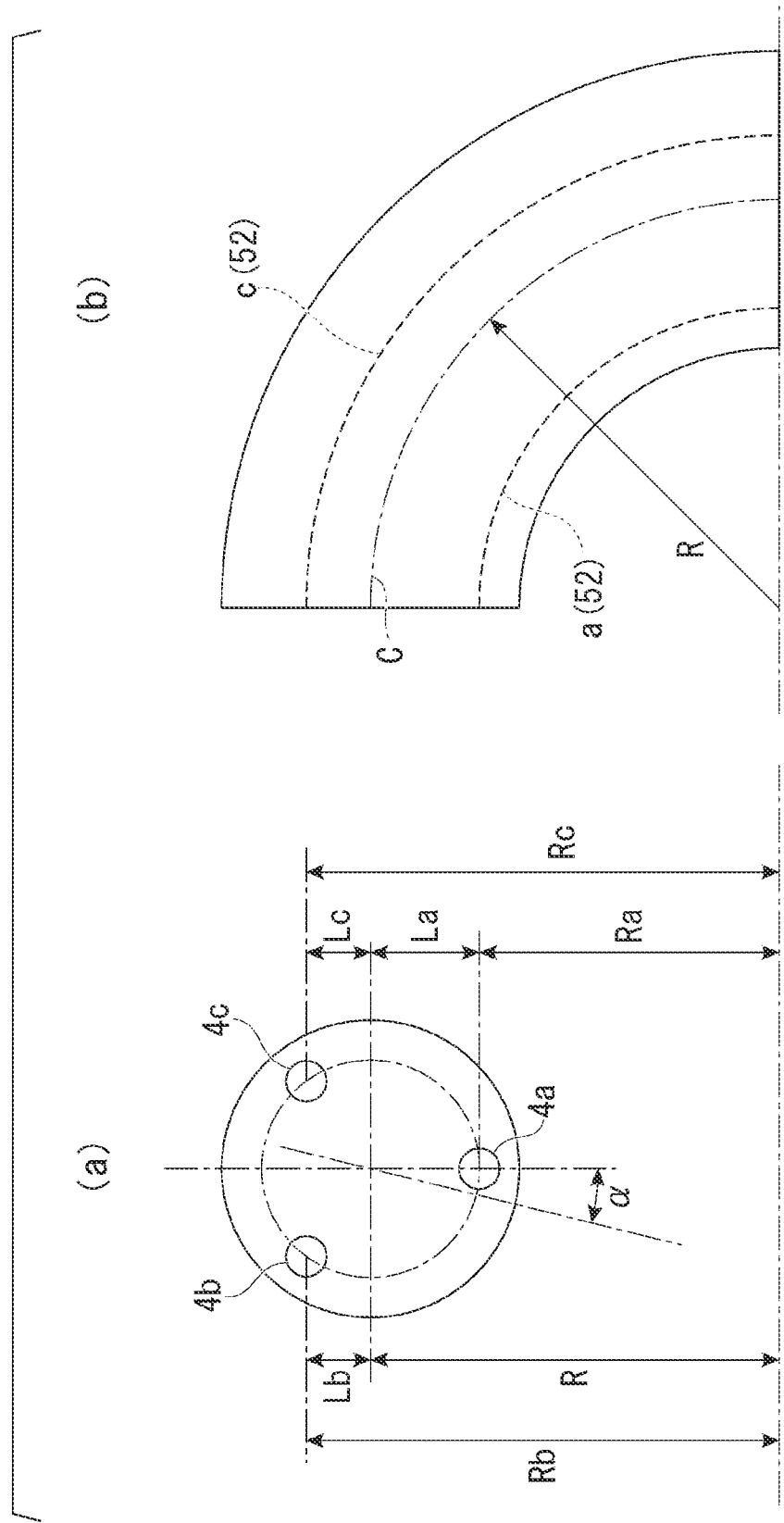

FIG. 4(a) is a cross-sectional view of the insertion unit 1. FIG. 4(b) is a cross-sectional view of the insertion unit 1. The bending portion 3 shown in FIG. 4 bends according to the parameters shown in Table 1.

TABLE 1

| Item | Symbol |
| --- | --- |
| Radius of curvature of central axis C of insertion unit 1 | R |
| Bending angle | θ |
| Wire PCD | Dw |
| Rotation angle of wire a with respect to bending angle | α |

As shown in FIG. 4(a), the distance between the wire a and the central axis C of the insertion unit 1 in a bending direction is defined as "La." Similarly, the distance between the wire b and the central axis C of the insertion unit 1 in a bending direction is defined as "Lb." Similarly, the distance between the wire c and the central axis C of the insertion unit 1 in a bending direction is defined as "L." La, Lb, and Lc are calculated as shown in Table 2.

TABLE 2

| | Central axis C of insertion unit 1 | Wire a | Wire b | Wire c |
| --- | --- | --- | --- | --- |
| Distance from central axis C of insertion unit 1 to center of each wire in bending direction | *** | La = (Dw/2) × cos(α) | Lb = (Dw/2) × cos(α + 120°) | Lc = (Dw/2) × cos(α + 240°) |
| Radius of curvature | R | Ra = R − La | Rb = R − Lb | Rc = R − Lc |
| Wire path length | W0 = (2 × | Wa = (2 × | Wb = (2 × | Wc = (2 × |

TABLE 2-continued

| | Central axis C of insertion unit 1 | Wire a | Wire b | Wire c |
|---|---|---|---|---|
| Change amount in wire path length | $\pi \times R) \times (\theta/360°)$ *** | $\pi \times Ra) \times (\theta/360°)$ $\Delta Wa = Wa - WO$ | $\pi \times Rb) \times (\theta/360°)$ $\Delta Wb = Wb - WO$ | $\pi \times Rc) \times (\theta/360°)$ $\Delta Wc = Wc - WO$ |

A radius of curvature "Ra" of the wire a, a radius of curvature "Rb" of the wire b, and a radius of curvature "Rc" of the wire c are calculated using La, Lb, and Lc as shown in Table 2.

The path length "Wa" of the wire a that is inserted into the insertion unit 1, the path length "Wb" of the wire b that is inserted into the insertion unit 1, and the path length "Wc" of the wire c that is inserted into the insertion unit 1 are calculated using Ra, Rb, and Rc as shown in Table 2. Further. ΔWa, ΔWb, and ΔWc are calculated using Wa, Wb, and Wc as shown in Table 2.

Figure 5:
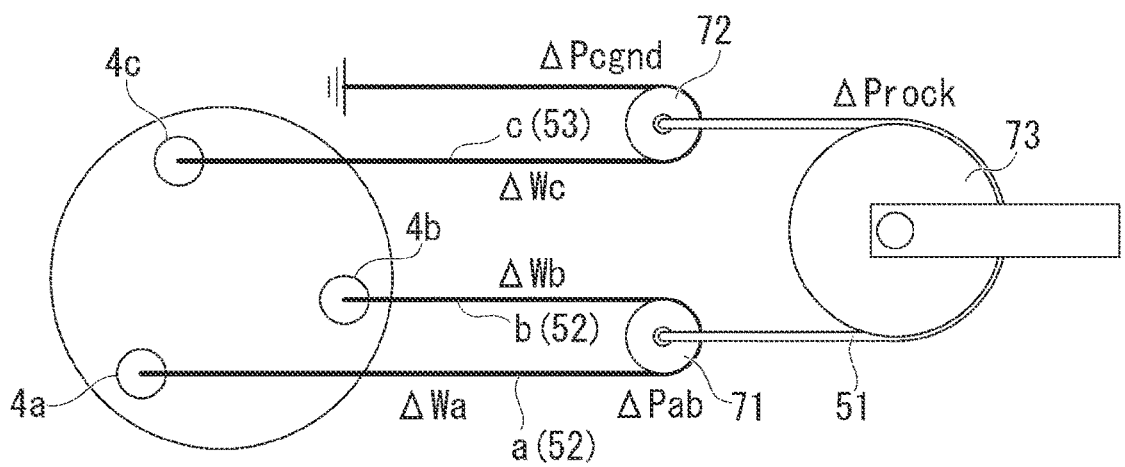
FIG. 5 is a view illustrating a relationship between change amounts in path lengths of a wire a, a wire b, and a wire c and the drive unit.

FIG. 5 is a view illustrating a relationship between change amounts of the path lengths of the three wires (the wire a, the wire b, and the wire c) and the drive unit 7.

In a case in which the path lengths of the three wires change, the first pulley 71 and the second pulley 72 move advance and retraction, that is, toward the distal end side or the proximal end side, while rotating around the rotation shaft to cancel the changes in the path lengths. The advance and retraction movement amount "ΔPab" of the first pulley 71 and the advance and retraction movement amount "ΔPcgnd" of the second pulley 72 are calculated as shown in Table 3.

TABLE 3

| Advance and retraction movement amount | First pulley 71 $\Delta Pab = (\Delta Wa + \Delta Wb)/2$ | Second pulley 72 $\Delta Pcgnd = (\Delta Wc)/2$ |
|---|---|---|

The advance and retraction movement amount "ΔProck" of the third pulley 73 which is generated by the advance and retraction movement of the first pulley 71 and the second pulley 72 is calculated as shown in Table 4.

TABLE 4

| Advance and retraction movement amount of third pulley 73 | $\Delta Prock = (\Delta Pab + \Delta Pcgnd)/2$ |
|---|---|

Figure 6:
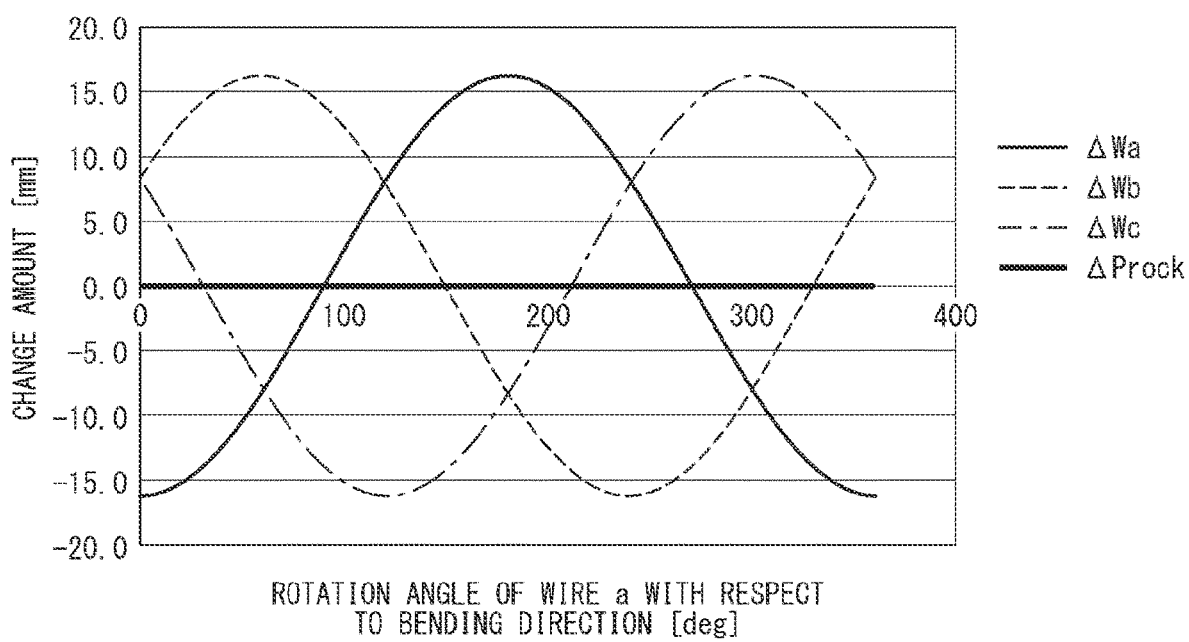
FIG. 6 is a graph showing calculation results of ΔWa, ΔWb, ΔWc, and ΔProck.

FIG. 6 is a graph showing calculation results of ΔWa, ΔWb, ΔWc, and ΔProck in a case in which α changes from 0 deg to 360 deg. The advance and retraction movement amount "ΔProck" of the third pulley 73 is zero regardless of α. That is, even in a case in which α changes, the third pulley 73 does not move advance and retraction. In other words, the position of the third pulley 73 does not change regardless of the bending direction of the insertion unit 1. Further, since the calculation results of FIG. 6 are obtained regardless of a value of a radius of curvature R when the insertion unit 1 bends, the position of the third pulley 73 does not change regardless of the bent shape of the insertion unit 1. That is, the position of the third pulley 73 does not change regardless of the direction or shape in which the insertion unit 1 bends.

[Multi-Lumen Tube 200]

A multi-lumen tube 200 is formed of a flexible material such as silicone. The multi-lumen tube 200 is inserted into the internal spaces of the flexible tube portion 2 and the bending pieces 31.

The multi-lumen tube 200 is provided with a fourth lumen 201 into which an observation means such as an endoscope is inserted, and a fifth lumen 202 and a sixth lumen 203 which each have an inner diameter smaller than that of the fourth lumen 201 and into each of which a treatment tool or the like is inserted, over the entire length. The fourth lumen 201, the fifth lumen 202, and the sixth lumen 203 are open on both the proximal end side and the distal end side.

By inserting the multi-lumen tube 200 into the overtube (medical device) 100, it is possible to configure a treatment system capable of treatment using an endoscope or a treatment tool.

The endoscope is inserted into the fourth lumen 201 of the multi-lumen tube 200, and the distal end of the insertion unit of the endoscope protrudes from the distal end of the overtube 100.

The treatment tool is inserted into the fifth lumen 202 or the sixth lumen 203 of the multi-lumen tube 200, and a gripping forceps or the like provided at the distal end of the insertion unit of the treatment tool protrudes from the distal end of the overtube 100.

[Operation of Medical Device 100]

Figure 7:
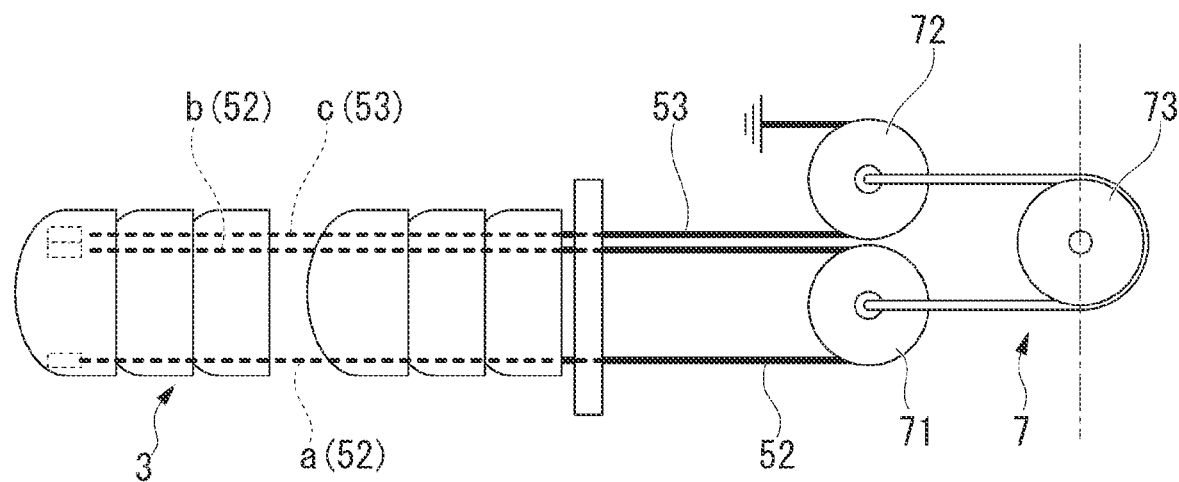
FIG. 7 is a schematic view illustrating an operation of the overtube.
Figure 8:
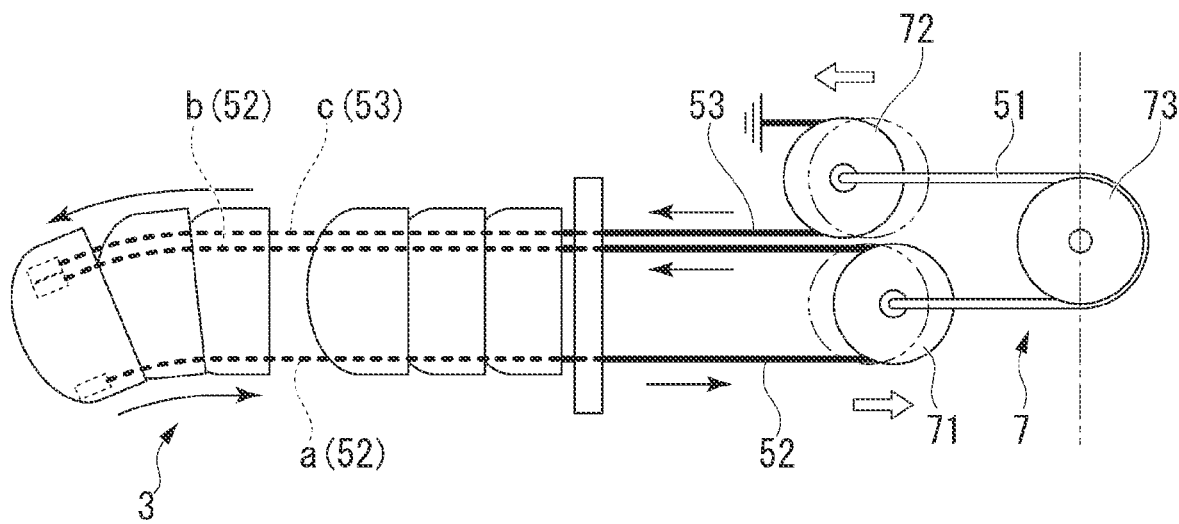
FIG. 8 is a schematic view illustrating an operation of the overtube.
Figure 9:
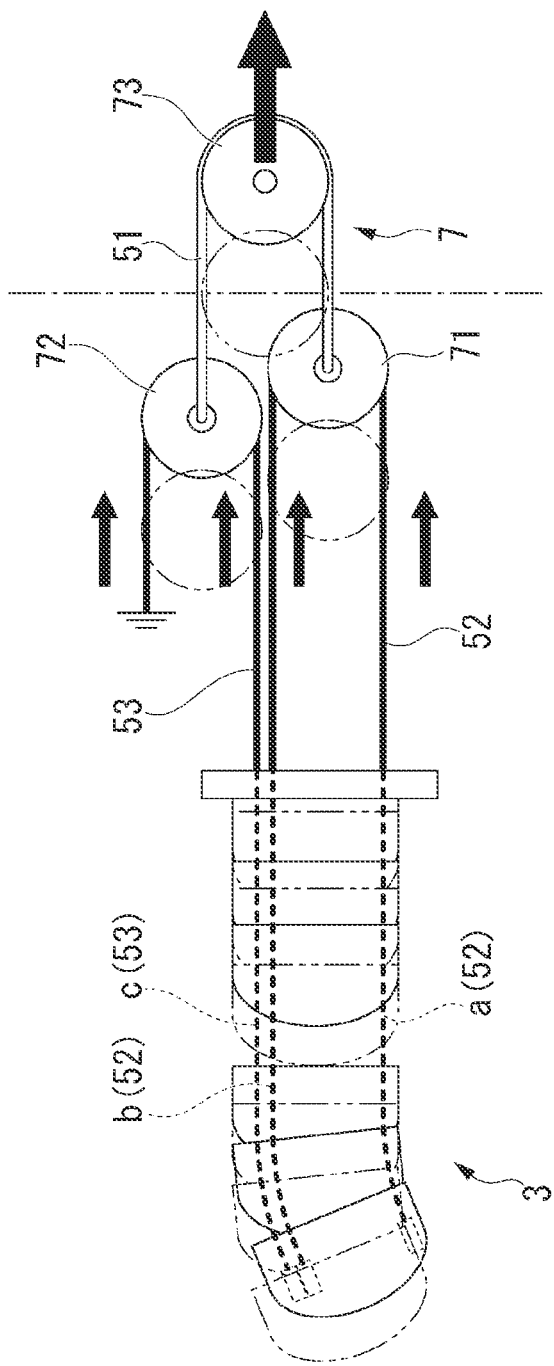
FIG. 9 is a schematic view illustrating an operation of the overtube.

Next, an operation of the overtube 100 will be described. Here, an operation of inserting the overtube 100 inside the large intestine L of the patient will be described. FIGS. 7 to 9 are schematic views illustrating the operation of the overtube 100.

First, the multi-lumen tube 200 is inserted into the main lumen 2a of the overtube 100, and the endoscope is inserted into the fourth lumen 201 of the multi-lumen tube 200 of the overtube 100.

As shown in FIG. 7, in a state in which the insertion unit 1 is not bent, the third wire 51, the first wire 52, and the second wire 53 are stretched without loosening.

Next, the endoscope having an active bending portion at the distal end thereof is inserted into the large intestine L of the patient. The operator inserts the distal end of the insertion unit of the endoscope into an affected portion of the large intestine L to be treated, while actively bending the active bending portion according to the shape of the bent portion of the large intestine L.

Next, the operator inserts the multi-lumen tube 200 and the overtube 100 along the endoscope. The bending portion 3 of the overtube 100 is inserted while bending along the bent shape of the endoscope.

As shown in FIG. 8, the path lengths (Wa, Wb, and Wc) change as the bending portion 3 bends. Due to the changes in the path lengths, the first pulley 71 and the second pulley 72 move advance and retraction, that is, toward the distal end side or the proximal end side, while rotating around the rotation shaft. In the example shown in FIG. 8, the first pulley 71 moves backward, that is, toward the proximal end side, and the second pulley 72 moves forward, that is, toward the distal end side. At this time, the third pulley 73 does not move advance and retraction. Further, the advance and retraction movement amount ΔPab of the first pulley 71 and the advance and retraction movement amount ΔPcgnd of the second pulley 72 are equal to each other. Therefore, it is easy to find the pull length of the wires to evenly pull the three wires (the wire a, the wire b, and the wire c). In the above description, it is described that the advance and retraction movement amount ΔPab of the first pulley 71 and the advance and retraction movement amount ΔPcgnd of the second pulley 72 are equal to each other, but, in reality, due to the influence of clearance, a frictional force, design error, or the like between inner walls of the three wire lumens 4 (the first lumen 4a, the second lumen 4b, and the third lumen 4c) and the three wires (the third wire 51, the first wire 52, and the second wire 53), the advance and retraction movement amount ΔPab of the first pulley 71 and the advance and retraction movement amount ΔPcgnd of the second pulley 72 may be extremely similar (substantially equal) to each other.

Next, the operator pulls the third pulley 73 toward the proximal end side. The operator pulls, for example, the wire attached to the rotation shaft of the third pulley 73. As shown in FIG. 9, the third pulley 73 moves toward the proximal end side. The third pulley 73 that moves toward the proximal end side pulls the first pulley 71 and the second pulley 72 toward the proximal end side. The advance and retraction movement amount of each of the first pulley 71 and the second pulley 72 substantially coincides with the advance and retraction movement amount of the third pulley 73.

The wire a, the wire b, and the wire c are pulled evenly by the advance and retraction movement amount of each of the first pulley 71 and the second pulley 72.

The three wires (the wire a, the wire b, and the wire c) are pulled toward the proximal end side, the bending pieces 31 are brought into close contact with each other, and frictional resistance acts between the bending pieces 31, and thus the bent shape of the bending portions 3 is held (fixed). That is, as the compressive force of the bending portion 3 in the longitudinal axis direction increases, a pressing force with which the bending pieces 31 are pressed increases, and the frictional resistance between the bending pieces 31 increases, and thus the stiffness changes.

As shown in FIG. 1, each of the bending pieces 31 is formed in a dome shape at the distal end side of the bending portion 3 in the longitudinal axis direction. In the bending portion 3 constituted by such bending pieces 31, it is possible to increase the contact area between the adjacent bending pieces 31 as much as possible when the bending pieces 31 move relative to each other and the entire bending portion 3 bends. By increasing the contact area between the adjacent bending pieces 31, it is possible to increase the frictional resistance acting between the bending pieces 31.

According to the overtube 100 that is a medical device according to the present embodiment, the three wires can be pulled evenly, and the bent shape of the bending portion 3 can be suitably held (fixed). Regardless of the bent posture of the bending portion 3, by only pulling the third pulley 73 toward the proximal end side, it is possible to evenly pull the three wires (the wire a, the wire b, and the wire c).

The first embodiment of the present invention has been described above in detail with reference to the drawings, but the specific configuration is not limited to this embodiment and includes a design change or the like without departing from the scope of the present invention. In addition, the components shown in the above-described embodiment and a modification example shown below can be appropriately combined and configured.

Modification Example 1

For example, in the above embodiment, the insertion unit 1 has the flexible tube portion 2 and the bending portion 3, but the aspect of the insertion unit is not limited to this. The insertion unit may be constituted by only the bending portion 3 without the flexible tube portion 2.

Second Embodiment

A second embodiment of the present invention will be described with reference to FIG. 10. In the following description, the same components as those already described will be designated by the same reference numerals and redundant description will be omitted. An overtube 100B according to the second embodiment is different from the overtube 100 according to the first embodiment in that the multi-lumen tube 200 is not inserted into the insertion unit.

[Overtube (Medical Device) 100B]

The overtube (a medical device) 100B includes an insertion unit 1B, the operation unit 6 provided at a proximal end of the insertion unit 1B, and the drive unit 7 having a third wire 51, a first wire 52, and a second wire 53.

The insertion unit 1B is a long member that is inserted into the body. The insertion unit 1B has a bendable bending portion 3B provided on a distal end side thereof and a flexible tube portion 2B that is connected to the bending portion 3B and extends to a proximal end side thereof.

The flexible tube portion 2B is a tubular member formed of a flexible material such as silicone.

The bending portion (a variable stiffness portion) 3B is constituted by a plurality of bending pieces 31B disposed side by side in an axial direction and is provided at a distal end of the flexible tube portion 2B. The stiffness of the bending portion 3B changes with the compressive force in a longitudinal axis direction.

The bending piece 31B is a short cylindrical member and an internal space thereof is open at both ends. The plurality of bending pieces 31B are superposed such that the internal spaces of the adjacent bending pieces 31B form a continuous space. An observation means such as an endoscope, a treatment tool, or the like is inserted into the continuous internal space.

Figure 10:
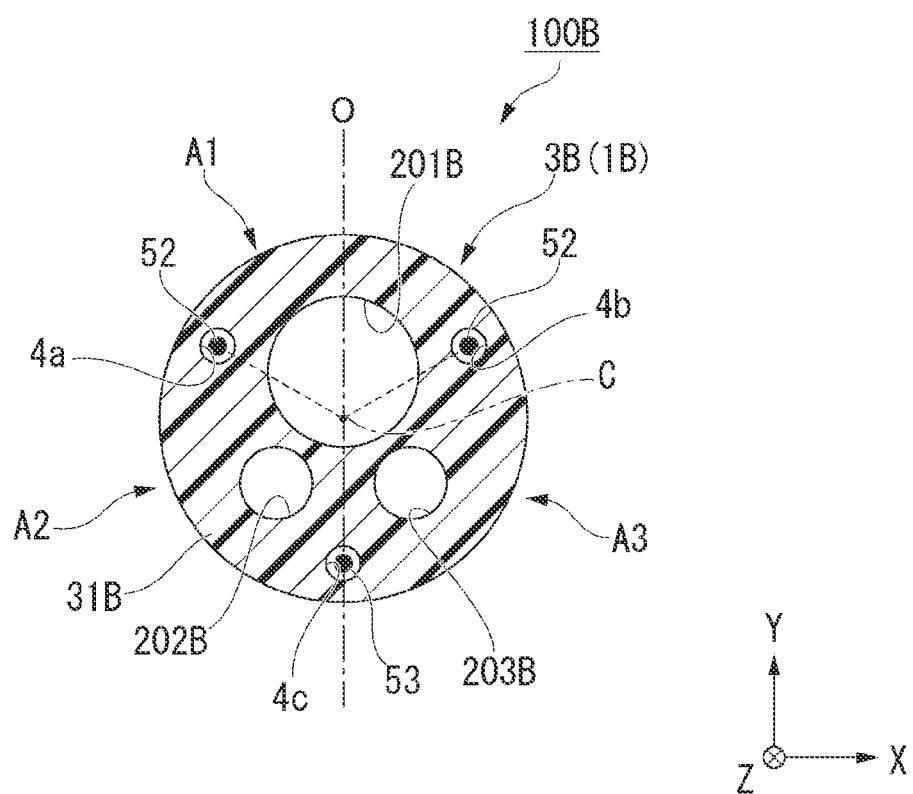
FIG. 10 is a cross-sectional view of an insertion unit of an overtube according to a second embodiment of the present invention.

FIG. 10 is a cross-sectional view perpendicular to the longitudinal axis of the bending portion 3B of the insertion unit 1B.

As shown in FIG. 10, three wire lumens 4 (a first lumen 4a, a second lumen 4b, a third lumen 4c) are disposed in the insertion unit 1B (the flexible tube portion 2B and the bending portion 3B) at intervals in a circumferential direction around the longitudinal axis of the insertion unit 1B. The wire lumen 4 is an internal space into which a wire can be inserted. As shown in FIG. 10, the three wire lumens 4 are disposed at positions where a circumference around the longitudinal axis of the insertion unit 1B is substantially equally divided. Further, distances from the central axis C to the three wire lumens 4 are substantially the same.

The first wire 52 and the second wire 53 are inserted into the wire lumen 4 of all the bending pieces 31B and the flexible tube portion 2B.

Further, as shown in FIG. 10, the insertion unit 1B (the flexible tube portion 2B and the bending portion 3B) is provided with a fourth lumen 201B that is an internal space into which an observation means such as an endoscope can be inserted, a fifth lumen 202B and a sixth lumen 203B which each have an inner diameter smaller than that of the fourth lumen 201B and are internal spaces into each of which a treatment tool or the like can be inserted, separately.

As shown in FIG. 10, in a cross section perpendicular to the longitudinal axis direction of the insertion unit 1B, the fifth lumen 202B and the sixth lumen 203B are symmetrically disposed with respect to an axis O passing through a center of the fourth lumen 201B and a center of any one of the three wire lumens 4. Further, the other two wire lumens 4 that are not on the axis O are also symmetrically disposed with respect to the axis O.

A region defined between a line segment connecting the first lumen 4a and a longitudinal axis C of the insertion unit 1B and a line segment passing through the second lumen 4b and the longitudinal axis of the insertion unit 1B is referred to as "a first region A1."

A region defined between a line segment connecting the first lumen 4a and a longitudinal axis C of the insertion unit 1B and a line segment passing through the third lumen 4c and the longitudinal axis of the insertion unit 1B is referred to as "a second region A2."

A region defined between a line segment connecting the second lumen 4b and a longitudinal axis C of the insertion unit 1B and a line segment passing through the third lumen 4c and the longitudinal axis of the insertion unit 1B is referred to as "a third region A3."

As shown in FIG. 10, the center of each of the fourth lumen 201B, the fifth lumen 202B, and the sixth lumen 203B is disposed in any one of the first region A1, the second region A2, and the third region A3 without overlap.

According to the overtube 100B that is a medical device according to the present embodiment, similarly to the overtube 100 of the first embodiment, the three wires can be pulled evenly, and the bent shape of the bending portion 3B can be suitably held (fixed).

According to the overtube 100B that is a medical device according to the present embodiment, as described above, the center of each of the fourth lumen 201B, the fifth lumen 202B, and the sixth lumen 203B is disposed in any one of the first region A1, the second region A2, and the third region A3 without overlap, and thus it is possible to reduce the outer diameter of the insertion unit 1B. That is, the fourth lumen 201B, the fifth lumen 202B, and the sixth lumen 203B are each disposed in spaces between the first lumen 4a, the second lumen 4b, and the third lumen 4c in the circumferential direction of the longitudinal axis C, and thus it is possible to minimize the outer diameter of the insertion unit 1B.

As described above, the second embodiment of the present invention has been described in detail with reference to the drawings, but the specific configuration is not limited to this embodiment and includes a design change or the like without departing from the scope of the present invention. In addition, the components shown in the above-described embodiment and modification example can be appropriately combined and configured.

What is claimed is:

1. A medical device comprising:
   an insertion unit; and
   a drive unit provided proximally relative to the insertion unit,
   wherein the insertion unit has first, second, and third lumens,
   the drive unit comprising:
      first, second and third pulleys, each disposed to be movable distally and proximally,
      first, second, and third wires wound on the first, second and third pulleys, respectively,
   the first wire comprising:
      a first portion located in the first lumen;
      a first end fixed to a distal end side of the insertion unit;
      a second portion located in the second lumen; and
      a second end fixed to the distal end side of the insertion unit,
   the second wire comprising:
      a third portion located in the third lumen;
      a third end fixed to the distal end side of the insertion unit, and
      a fourth end fixed to the drive unit,
   the third wire comprising:
      a fifth end fixed to the first pulley; and
      a sixth end fixed to the second pulley, and
   the third pulley is configured to move distally and proximally to pull each of the first wire and the second wire.

2. The medical device according to claim 1, wherein the first lumen, the second lumen, and the third lumen are disposed at equal intervals in a circumferential direction around a longitudinal axis of the insertion unit, and distances from the longitudinal axis to the first lumen, the second lumen, and the third lumen are equal to each other.

3. The medical device according to claim 2, wherein the first pulley and the second pulley is configured to move distally and proximally with bending of the insertion unit, and a movement amount of the first pulley and a movement amount of the second pulley are substantially equal to each other.

4. The medical device according to claim 1,
   wherein the insertion unit includes a variable stiffness portion, the stiffness of which is configured to change with a compressive force in the longitudinal axis direction, and
   wherein first and second ends of the first wire and the third end of the second wire are fixed to a distal end side of the variable stiffness portion.

5. The medical device according to claim 4,
   wherein the variable stiffness portion has a plurality of pieces into which the first wire and the second wire are inserted and which is movable in the longitudinal axis direction, and
   wherein, when the first wire and the second wire are pulled toward the proximal end side and the plurality of pieces are brought into close contact with each other, the stiffness of the variable stiffness portion changes.

6. A treatment system comprising:
   an endoscope;
   a multi-lumen tube having a fourth lumen, a fifth lumen, and a sixth lumen, wherein the fourth lumen is configured to receive the endoscope; and
   the medical device according to claim 1,
   wherein the insertion unit has a main lumen configured to receive the multi-lumen tube.

7. A treatment system comprising:
   an endoscope; and
   the medical device according to claim 1,
   wherein the insertion unit of the medical device includes a fourth lumen configured to receive the endoscope, a fifth lumen, and a sixth lumen.

8. The treatment system according to claim 7, wherein, in a cross section perpendicular to the longitudinal axis direction of the insertion unit, the fifth lumen and the sixth lumen are disposed symmetrically with respect to an axis passing through a center of the fourth lumen and a center of any one of the first lumen, the second lumen, and the third lumen, and any two of the first lumen, the second lumen, and third lumen which are not on the axis are symmetrically disposed with respect to the axis.

9. The treatment system according to claim 8, wherein, in a cross section perpendicular to the longitudinal axis direction of the insertion unit, the center of each of the fourth lumen, the fifth lumen, and the sixth lumen is disposed in any one of a first region defined between a line segment connecting the first lumen and the longitudinal axis of the insertion unit and a line segment passing through the second lumen and the longitudinal axis of the insertion unit, a second region defined between a line segment connecting the first lumen and the longitudinal axis of the insertion unit and a line segment passing through the third lumen and the longitudinal axis of the insertion unit, and a third region defined between a line segment connecting the second lumen and the longitudinal axis of the insertion unit and a line segment passing through the third lumen and the longitudinal axis of the insertion unit.

10. The medical device according to claim 1, wherein
the insertion unit includes a bending portion configured to be bent,
the bending portion has a first stiffness in a first state, and
the bending portion has a second stiffness in a second state, the second stiffness is stiffer than the first stiffness.

11. The medical device according to claim 10, wherein
the third pulley is located at a first location in the first state,
the third pulley is located at a second location in the second state, and
the third pulley is configured to move proximally from the first location to the second location in a longitudinal axis direction.

12. The medical device according to claim 11, wherein the first pulley is configured to move proximally when the third pulley moves proximally from the first location to the second location.

13. The medical device according to claim 12, wherein the second pulley is configured to move proximally when the third pulley moves proximally from the first location to the second location.

14. The medical device according to claim 10, wherein
the bending portion comprises a plurality of pieces,
adjacent pieces of the plurality of pieces each have a first friction resistance between each other in the first state,
adjacent pieces of the plurality of pieces each have a second friction resistance between each other in the second state, and
the second friction resistance is larger than the first friction resistance.

15. The medical device according to claim 14, wherein
the third pulley is located at a first location in the first state,
the third pulley is located at a second location in the second state, and
the third pulley is configured to move proximally from the first location to the second location in a longitudinal axis direction.

16. The medical device according to claim 10, wherein the third pulley is configured to fix a bent shape of the bending portion.

17. The medical device according to claim 11, wherein the third pulley is configured to fix a bent shape of the bending portion.

18. The medical device according to claim 1, wherein the first portion is different from the second portion.

19. The medical device according to claim 1, wherein the first lumen, the second lumen, and the third lumen are disposed at intervals in a circumferential direction around a longitudinal axis of the insertion unit.

* * * * *